United States Patent [19]

Heid et al.

[11] Patent Number: 5,028,638

[45] Date of Patent: Jul. 2, 1991

[54] HYBRID PLASTIC FILLING MATERIAL

[75] Inventors: Renate Heid, Edingen; Jens Winkel, Koeln; Heiko Herold, Neuss; Peter Schwabe, Leverkusen; Werner Finger, Dormagen; Wolfgang Podszun, Koeln, all of Fed. Rep. of Germany

[73] Assignee: Bayer Aktiengesellschaft, Leverkusen, Fed. Rep. of Germany

[21] Appl. No.: 468,049

[22] Filed: Jan. 22, 1990

[30] Foreign Application Priority Data

Feb. 9, 1989 [DE] Fed. Rep. of Germany ....... 3903734

[51] Int. Cl.$^5$ .......................... C08K 3/40; C08L 33/08; C08L 33/10
[52] U.S. Cl. ........................................ 522/14; 522/17; 522/77; 522/908; 523/109; 524/847
[58] Field of Search ...................... 522/77, 14, 17, 908

[56] References Cited

U.S. PATENT DOCUMENTS

| | | | |
|---|---|---|---|
| 4,089,763 | 5/1978 | Dart et al. | 522/908 |
| 4,437,836 | 3/1984 | Schmitz-Josten et al. | 522/17 |
| 4,544,359 | 10/1985 | Waknine | 522/14 |

FOREIGN PATENT DOCUMENTS

| | | |
|---|---|---|
| 060911 | 9/1982 | European Pat. Off. |
| 073995 | 3/1983 | European Pat. Off. |
| 0166009 | 1/1986 | European Pat. Off. |

Primary Examiner—Marion E. McCamish
Assistant Examiner—Susan Berman
Attorney, Agent, or Firm—Sprung, Horn, Kramer & Woods

[57] ABSTRACT

In a dental composite containing a polymerizable (meth)acrylic compound, photoinitiator, accelerator, inorganic filler and conventional auxiliaries, the improvement wherein the composite by weight comprises about (a) 10-50% of at least one monomer which contains at least 2 polymerizable (meth)acrylic acid groups,
(b) 5-80% of a glass or a glass ceramic which has an average particle size of between about 0.1 and 10 μm and has been post-treated with γ-methacryloxypropyltrimethoxysilane up to a carbon content of between about 0.5 and 2.5% by weight,
(c) 2-10% of a surface-treated microfiller and
(d) 0.1-5% of a photoactivator consisting of a mixture of camphorquinone and p-dialkylaminobenzenesulphonamide. The composition has a long pot life and good surface color when cured.

2 Claims, No Drawings

HYBRID PLASTIC FILLING MATERIAL

The invention relates to new light-curing dental composites, in particular tooth filling composites.

Light-curing tooth filling materials are known. They consist in general of one or more (meth)acrylic resins, surface-treated fillers, photoactivators, accelerators and auxiliaries (e.g. colorants, light stabilizers, stabilizers and the like). Filling materials are divided into those which are used in the anterior teeth and those which are used in the posterior teeth. The latter frequently contain large amounts of inorganic filler to achieve sufficient wear resistance and good mechanical properties.

An essential requirement for a suitable material is a sufficiently long pot life under ambient light (daylight).

The dentist must have enough time available to insert the material in the cavity and shape it there as he sees fit. Even during an extended duration of treatment by the dentist, for example in edge construction, the plastic filling material must not become solid under ambient light.

On the other hand, rapid and complete curing of the filling is expected to take place on exposure to the light of a dental lamp. The polymerization depths must thus be as large as possible and, at the same time, no inhibition layer must form on the surface of the material.

At present, no composites are known which meet both requirements.

Many of the known filling materials have a pot life which is much too short. If these materials are subjected to a test, such as, for example, provided by DIN proposal 0013922, they are often only processable up to 10 seconds. This is much too short, especially for fillings in the molar area, since there is a risk that the material is cured or partially polymerized during the processing and thus is damaged in a way not always discernible to the dentist. Other materials have an adequate pot life, but these form a deep inhibition layer at the surface. When the materials are subjected to a test such as provided by the "Revision of ISO 4049, 1978", these materials show substantial discolorations on the surface. Moreover, the curing behavior of the filling materials often deteriorates even after a very short shelf-life, and the dentist has no guarantee that they will cure completely.

The object of the present invention is to provide a storable light-curable plastic filling material, in the use of which, on the one hand, there is sufficient time to allow the material to be carefully placed, but which, on the other hand, is also cured rapidly and completely upon exposure to the light of a commercial dental lamp.

It has been found that the use of p-dialkylaminobenzenesulphonamides as accelerators, together with camphorquinone in combination with surface-coated glass fillers of a certain degree of silanization, and microfillers and commercial monomers and auxiliaries leads to filling materials which have a long pot life but, on the other hand, cure rapidly and completely after exposure to the light of a dental lamp. Compared with known products, these materials do not show any deterioration in mechanical properties after storage for 2 years.

The light-curing dental composites according to the invention, in particular tooth filling composites, which contain one or more polymerizable (meth)acrylic compounds, photoinitiators, accelerators, inorganic fillers and, if desired, conventional auxiliaries are characterized in that they contain:

a) 10–50% by weight of one or more monomers which contain at least 2 polymerizable (meth)acrylic acid groups,
b) 5–80% by weight of a glass or a glass ceramic which has an average particle diameter of between 0.1 and 10 $\mu$m and has been surface-treated with $\gamma$-methacryloxypropyltrimethoxysilane up to a carbon content of between 0.2 and 2.5% by weight,
c) 2–10% by weight of a surface-treated microfiller and
d) 0.1–5% by weight of a photoactivator consisting of a mixture of camphorquinone and p-dialkylaminobenzenesulphonamide.

Examples of suitable monomers are as follows:

Triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis(p-(2'-hydroxy-3'-methacryloyloxypropoxy)phenyl)propane, 2,2-bis(p-(2,-methacryloyloxyethoxy)phenyl)propane, trimethylolpropane tri(meth)acrylate, bis-(meth)acryloyloxymethyl)-tricyclo-[5.2.2.0$^{2.6}$]decane according to German Offenlegungsschrift 2,931,925 and German Offenlegungsschrift 2,931,926, 1,3-di((meth)acryloyloxypropyl)-1,1,3,3-tretramethyldisiloxane and 1,3-bis(3-(meth)acryloyloxyethylcarbamoyloxypropyl)-1,1,3,3-tetramethyldisiloxane. Monomers which at 13 mbar have a boiling point of more than 100° C. are particularly preferred.

In the context of the present invention, it is preferred to use mixtures of different (meth)acrylates according to the invention.

It is also possible to use mixtures of monomers which contain several comonomers.

Preferred light-curing dental composites according to the invention, in particular tooth filling composites, which contain one or more polymerizable (meth)acrylic compounds, photoinitiators, accelerators, inorganic fillers and, if desired, conventional auxiliaries are characterized in that they contain a) 10–30% by weight of one or more monomers which contain at least 2 polymerizable (meth)acrylic acid groups,
b) 40–75% by weight of a glass or a glass ceramic which has a particle size of between 0.1 and 10 $\mu$m and has been post-treated with $\gamma$-methacryloxypropyltrimethoxysilane up to a carbon content of between 0.5 and 2.5% by weight,
c) 2–10% by weight of a surface-treated microfiller and
d) 0.1–5% by weight of a photoactivator consisting of a mixture of camphorquinone and p-dialkylaminobenzenesulphonamide.

The examples which follow demonstrate the advantages of the composites according to the invention.

As already mentioned, the essential feature of a plastic filling material is a sufficiently long pot life in combination with rapid and complete curing on exposure to the light of a dental lamp. This means that the polymerization depths should be as large as possible. An inhibition layer on the surface of the cured plastic, which becomes visible as a strong surface discoloration in a test according to "Revision of ISO 4049/1978", is a disadvantage; it must be avoided. Thus, the optimum composite should have long pot lives in ambient light, rapid and complete curing on exposure to the light of a dental lamp and no surface discoloration. This requirement is met by the plastic filling materials according to the invention.

EXAMPLE 1 (COMPARATIVE EXAMPLE)

1000 g of paste contain:
Bisphenol-A diglycidyl dimethacrylate (BIS GMA): 128.725 g
Triethylene glycol dimethacrylate (TEGDMA): 105.330 g
Surface-treated Ba glass filler, average particle diameter 1.3 μm: 762.225 g
Camphorquinone/diethylaminoethyl acrylate as starter system: 1.010 g
Auxiliaries and additives: 2.710 g
(2.38 g of ®TINUVIN P, 0.33 g of ®IONOL) Pot life of the paste in ambient light measured in accordance with DIN proposal 0013922: 150 s
Polymerization depth after an exposure of 60 s to the light of a dental lamp: 6.5 mm
Inhibition layer on the surface of the cured plastic filling material determined by a test as provided in "Revision of ISO 4049/1978": yes

EXAMPLE 2 (COMPARATIVE EXAMPLE)

1000 g of paste contain:
BIS GMA: 62.00 g
TEGDMA: 62.00 g
Surface-treated Zn glass filler, average particle diameter 2.3 μm: 875.00 g
Auxiliaries and additives: 1.44 g
(1.26 g of ®TINUVIN P, 0.18 g of ®IONOL) Camphorquinone N,N-dimethylamino-p-hydroxyethylbenzene as starter system: 1.30 g
Pot life of the paste in ambient light measured in accordance with DIN proposal 0013922: 50 s
Polymerization depth after an exposure of 60 s to the light of a dental lamp: 5.9 mm
Inhibition layer on the surface of the cured plastic filling material determined by a test as provided in "Revision of ISO 4049/1978": yes

EXAMPLE 3 (COMPARATIVE EXAMPLE)

1000 g of paste contain:
BIS phenol-A PO/hexamethylene diisocyanate: 74.25 g
TEGD-MA: 60.75 g
Surface-treated Ba glass filler, average particle diameter 3 μm: 862.03 g
Auxiliaries and additives: 1.56 g
(1.37 g of ®TINUVIN P, 0.19 g of ®IONOL) Camphorquinone/diethylaminoethyl methacrylate as starter system: 1.41 g
Pot life of the paste in ambient light measured in accordance with DIN proposal 0013922: 30 s
Polymerization depth after an exposure of 60 s to the light of a dental lamp: 6.5 mm
Inhibition layer on the surface of the cured plastic filling material determined by a test as provided in "Revision of ISO 4049/1978": no

EXAMPLE 4 (COMPARATIVE EXAMPLE)

1000 g of paste contain:
BIS GMA: 71.00 g
TEGDMA: 71.00 g
Surface-treated Zr ceramic filler, average particle diameter 2 μm: 854.83 g
Auxiliaries and additives: 1.65 g
(1.45 g of ®TINUVIN P, 0.20 g of ®IONOL) Camphorquinone N,N-dimethylamino-p-hydroxyethylbenzene (present in the monomer): 1.52 g
Pot life of the paste in ambient light measured in accordance with DIN proposal 0013922: 15 s
Polymerization depth after an exposure of 60 s to the light of a dental lamp: 4.7 mm
Inhibition layer on the surface of the cured plastic filling material determined by a test as provided in "Revision of ISO 4049/1978": no

EXAMPLE 5 (ACCORDING TO THE INVENTION)

1000 g of paste contain:
BIS GMA: 172.015 g
TEGDMA: 74.008 g
Surface-treated Ba glass filler, average particle diameter 1.2 μm: 749.486 g
Camphorquinone/diallylsulphonamide as starter system: 1.641 g
Auxiliaries and additives: 2.850 g
(2.50 g of ®TINUVIN P, 0.35 g of ®IONOL) Pot life of the paste in ambient light measured in accordance with DIN proposal 0013922: 100 s
Polymerization depth after an exposure of 60 s to the light of a dental lamp: 7.7 mm
Inhibition layer on the surface of the cured plastic filling material determined by a test as provided in "Revision of ISO 4049/1978": no The examples listed clearly show that the composite according to the invention (Example 5) which contains the new starter system camphorquinone/diallylsuphonamide in combination with the surface-coated glass fillers of a certain degree of silanization meets the required conditions. In addition to a long pot life in ambient light, rapid and complete curing is achieved on exposure to the light of a dental lamp, while the cured plastic filling material does not show a surface discoloration.

The material according to comparative Example 1 has a very long pot life in ambient light, but the curing depths on exposure to the light of a dental lamp are small and at the same time a thick inhibition layer is formed on the surface of the cured material.

The materials according to Examples 2, 3 and 4 have very short pot lives under ambient light.

The weight ratio of camphorquinone to diallylsulphonamide advantageously is from 4:1 to 1:4 and preferably from 2:1 to 1:2.

It will be appreciated that the instant specification and claims are set forth by way of illustration and not limitation and that various modifications and changes may be made without departing from the spirit and scope of the present invention.

What is claimed is:

1. In a dental composite containing a polymerizable (meth)acrylic compound, photoinitiator, accelerator, inorganic filler and conventional auxiliaries, the improvement wherein the composite by weight consisting essentially of about (a) 10–50% of at least one monomer selected from the group comprising triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis(p-(2'-hydroxy-3'-methacryloyloxypropoxy) phenyl)propane, 2,2-bis(p-(2'-methacryloyloxyethyoxy)phenyl)propane, trimethylolpropane tri(- meth)acrylate, bis-(meth)acryloyloxymethyl)tricyclo-[5.2.1.0$^{2.6}$] decane, 1,3-di((meth) acryloyloxypropyl)-1,1,3,3-tretramethyl-disiloxane and 1,3-bis(3-(meth)acryloyloxyethylcarbamoyloxypropyl)-1,1,3,3-tetramethyldisiloxane, (b) 5–80% of a glass or a glass ceramic which has an average particle size of between about 0.1 and 10 um and has been post-treated with y-methacryloxypropyltrimethoxysilane up to a carbon content of between about 0.5 and 2.5% by weight, and (c) 0.1–5% of a photoactivator consisting of a mixture of camphorquinone and p-dialkylaminobenzenesulphonamide.

2. A dental composite according to claim 1, by weight consisting essentially of about (a) 10–30% of at least one monomer selected from the group comprising triethylene glycol dimethacrylate, tetraethylene glycol dimethacrylate, 1,12-dodecanediol dimethacrylate, 1,6-hexanediol dimethyacrylate, diethylene glycol dimethacrylate, 2,2bis(p-(2'-hydroxy-3'-methacryloyloxypropoxy)-phenyl)propane, 2,2-bis(p-(2'-methacryloyloxyethoxy)phenyl)propane, trimethylolpropane tri(meth)acrylate, bis-(meth)acryloyloxymethyl)-tricyclo-[5.2.1.0$^{2.6}$]decane, 1,3-di((meth)acryloyloxypropyl)-1,1,3,3-tretramethyldisiloxane and 1,3-bis(3-(meth)acryloyloxyethylcarbamoyloxypropyl)-1,1,3,3-tetramethyldisiloxane, (b) 40–75% of a glass or a glass ceramic which has an average particle size of between about 0.1 and 10 um and has been post-treated with y-methacryloxypropyltrimethoxysilane up to a carbon content of between about 0.5 and 2.5% by weight, and (c) 0.1–5% of a photoactivator consisting of a mixture of camphorquinone and p-dialkylaminobenzenesulphonamide.

* * * * *

UNITED STATES PATENT AND TRADEMARK OFFICE
CERTIFICATE OF CORRECTION

PATENT NO. : 5,028,638

DATED : July 2, 1991

INVENTOR(S) : Heid et al.

It is certified that error appears in the above-identified patent and that said Letters Patent is hereby corrected as shown below:

Col. 4, lines 67-68    Delete " methacryloyloxyethyoxy " and substitute -- methacryloyloxyethoxy --

Col. 6, line 1    Delete " thyacrylate " and substitute -- thacrylate --

Signed and Sealed this

Twenty-seventh Day of April, 1993

*Attest:*

MICHAEL K. KIRK

*Attesting Officer*      *Acting Commissioner of Patents and Trademarks*